(12) United States Patent
Liverton et al.

(10) Patent No.: US 6,214,823 B1
(45) Date of Patent: Apr. 10, 2001

(54) BENZODIAZEPINE DERIVATIVES AS ANTIARRHYTHMIC AGENTS

(75) Inventors: Nigel J. Liverton, Harleysville; John W. Butcher, Telford; David A. Claremon, Maple Glen; Harold G. Selnick, Ambler, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/167,065

(22) Filed: Oct. 6, 1998

Related U.S. Application Data

(60) Provisional application No. 60/062,833, filed on Oct. 17, 1997, now abandoned.

(51) Int. Cl.[7] .................. A61K 31/551; C07D 243/14
(52) U.S. Cl. ........................... 514/221; 540/509
(58) Field of Search ................ 540/509; 514/221

(56) References Cited

U.S. PATENT DOCUMENTS

| 4,628,084 | 12/1986 | Bock et al. | 540/509 |
|---|---|---|---|
| 4,994,258 | 2/1991 | Burns et al. | 424/1.1 |
| 5,004,741 | 4/1991 | Evans et al. | 514/221 |
| 5,426,185 | 6/1995 | Baldwin et al. | 540/509 |
| 5,595,900 | 1/1997 | Lowe | 435/193 |
| 5,597,818 | 1/1997 | Sanguinetti et al. | 514/221 |
| 5,631,251 | 5/1997 | Butcher et al. | 514/221 |
| 5,633,251 | 5/1997 | Claremon et al. | 514/221 |
| 5,658,901 | 8/1997 | Claremon et al. | 514/221 |
| 5,776,930 | 7/1998 | Lynch et al. | 514/221 |
| 5,817,658 | 10/1998 | Siegl et al. | 514/221 |

FOREIGN PATENT DOCUMENTS

WO 97/48686   12/1997   (WO).

OTHER PUBLICATIONS

Selnick, et al., J. Med. Chem., vol. 40, pp. 3865–3868, 1997.
Tokarski, et al., J. Med. Chem., vol. 37, pp. 3639–3654, 1994.
Bureau, et al., Eur. J. Med. Chem., vol. 29, pp. 487–494, 1994.

*Primary Examiner*—Richard L. Raymond
(74) *Attorney, Agent, or Firm*—Soonhee Jang; Valerie J. Camara; Mark R. Daniel

(57) ABSTRACT

This invention is concerned with novel compounds represented by structural formula I

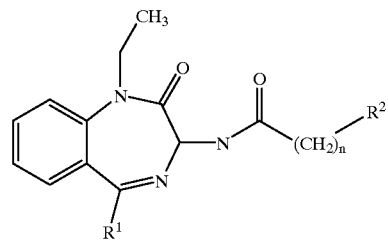

which are useful in the treatment of arrhythmia.

4 Claims, No Drawings

BENZODIAZEPINE DERIVATIVES AS ANTIARRHYTHMIC AGENTS

This application claims priority from provisional application U.S. Ser. No. 60/062,833, filed Oct. 17, 1997 (now abandoned).

BACKGROUND OF THE INVENTION

Arrhythmias often occur as complications to cardiac diseases such as myocardial infarction and heart failure. In serious cases, arrhythmias may give rise to ventricular fibrillation which can cause sudden death.

According to the classification of Vaughan-Williams, there are four distinct classes of antiarrhythmic agents. Class I antiarrhythmic agents are those agents which provide for sodium channel blockade, including those compounds which exert a membrane stabilizing effect. Exemplary of this class of compounds are quinidine, procainamide, disopyramide, lidocane, tocainide, flecainide and propafenone. Class II antiarrhythmic compounds are agents which block sympathetic activity. Exemplary of this class of compounds are propranolol and acebutolol. Class III antiarrhythmic agents are compounds which prolong the effective refractory period without altering the resting membrane potential or rate of depolarization. Compounds such as amiodarone, bretylium and sotalol are considered to be in this class. Class IV antiarrhythmic agents are effective in calcium channel blockade. Exemplary of this class of compounds are diltiazem and verapamil. Further definition of these classes can be found in Pharma Projects, section C1B, May 1993.

Though various antiarrythmic agents are now available on the market, agents which exhibit both satisfactory effects and high safety profiles have not been marketed, For example, antiarrythmic agents of Class I, which cause a selective inhibition of the maximum velocity of the upstroke of the action potential (Vmax), are inadequate for preventing ventricular fibrillation. In addition, they have problems regarding safety as they cause a depression of the myocardial contractility and have a tendency to induce arrythmias due to an inhibition of the impulse conduction. Beta-adrenoceptor blockers and calcium antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drugs which cause a selective prolongation of the duration of the action potential without a significant depression of the Vmax. Drugs in this class are limited. Drugs such as sotalol and amiodarone have been shown to possess Class III properties. Sotalol also possesses Class II effects which can cause cardiac depression and is therefore contraindicated in certain susceptible patients. Amiodarone is also severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

U.S. Pat. No. 5,658,901 discloses novel 2-oxo-1,4-benzodiazepines which are potent Class III agents. Compounds in this patent, while extremely potent, display extended half lives in animals, resulting in a high potential for toxicity. The compounds of the present invention show a decreased half-life in animals.

U.S. Pat. Nos. 5,595,900 and 5,631,251 disclose additional antiarrhythmic benzodiazepines.

SUMMARY OF THE INVENTION

This invention relates to compounds of the general formula

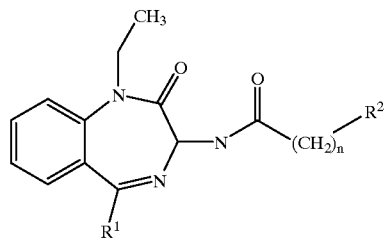

wherein $R^1$ is
1) phenyl,
2) substituted phenyl, with one or two substituents, selected from the group consisting of
   a) -hydrogen,
   b) —Cl, Br, F, or I,
   c) —$CF_3$,
   d) —$C_{1-3}$ alkyl,
   e) —$C_{1-3}$ alkoxy, or
3) cyclopropyl;

$R^2$ is
1) phenyl,
2) substituted phenyl, with one or two substituents, selected from the group consisting of
   a) -hydrogen,
   b) —Cl, Br, F, or I,
   c) —$CF_3$,
   d) —$C_{1-3}$ alkyl,
   e) —$C_{1-3}$ alkoxy, and n is 0, 1 or 2;

or a pharmaceutically acceptable addition salt and/or hydrate thereof, or crystal form thereof, or where applicable, a geometric or optical isomer or racemic mixture thereof.

The invention also relates to pharmaceutical compositions containing said compounds for use in mammals and methods of treating arrhythmia by the administration of one or a combination of the novel compounds of the invention.

DETAILED DESCRIPTION OF THE INVENTION

This invention relates to compounds of the general formula wherein
R¹ is
1) phenyl,
2) substituted phenyl, with one or two substituents, selected from the group consisting of
   a) -hydrogen,
   b) —Cl, Br, F, or I,
   c) —$CF_3$,
   d) —$C_{1-3}$ alkyl,
   e) —$C_{1-3}$ alkoxy, or
3) cyclopropyl;
R² is
1) phenyl,
2) substituted phenyl, with one or two substituents, selected from the group consisting of
   a) -hydrogen,
   b) —Cl, Br, F, or I,
   c) —$CF_3$,
   d) —$C_{1-3}$ alkyl,
   e) —$C_{1-3}$ alkoxy, and
n is 0, 1 or 2;
or a pharmaceutically acceptable addition salt and/or hydrate thereof, or crystal form thereof, or where applicable, a geometric or optical isomer or racemic mixture thereof.

The compounds of the present invention may have asymmetric centers and occur as racemates, mixtures of enantiomers, individual diastereomers, or as individual enantiomers with all isomeric forms being included in the present invention.

A preferred embodiment of this invention is represented by wherein
R² is
1) substituted phenyl, with one or two substituents, selected from the group consisting of
   a) -hydrogen,
   b) —Cl, Br, F, or I,
   c) —$CF_3$,
   d) —$C_{1-3}$ alkyl, and
n is 0, 1 or 2.

A second preferred embodiment of this invention is represented by wherein
R² is
1) substituted phenyl, with one or two substituents, selected from the group consisting of
   a) -hydrogen,
   b) —Cl, Br, F, or I,
   c) —$CF_3$,
   d) —$C_{1-3}$ alkyl, and
n is 0, 1 or 2.

Unless otherwise stated or indicated, the following definitions shall apply throughout the specification and claims.

When any variable occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentane, isohexane, etc.

The term "halogen" or "halo" is intended to include fluorine, chlorine, bromine and iodine.

As used herein, the term "composition" is intended to encompass a product comprising the specified ingredients in the specified amounts, as well as any product which results, directly or indirectly, from combination of the specified ingredients in the specified amounts.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of the invention are prepared by the following reaction schemes. All substituents are as defined above unless indicated otherwise.

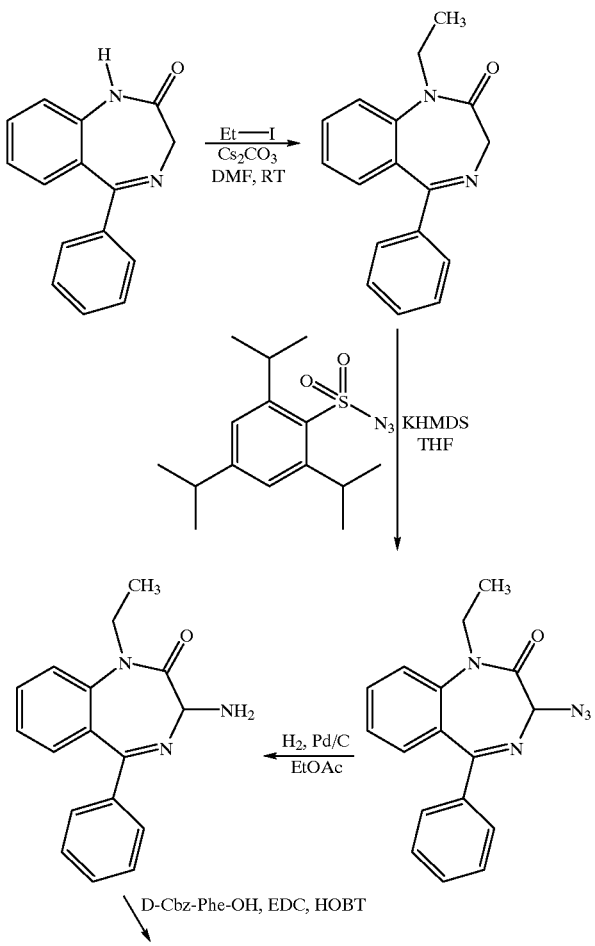

Scheme 1

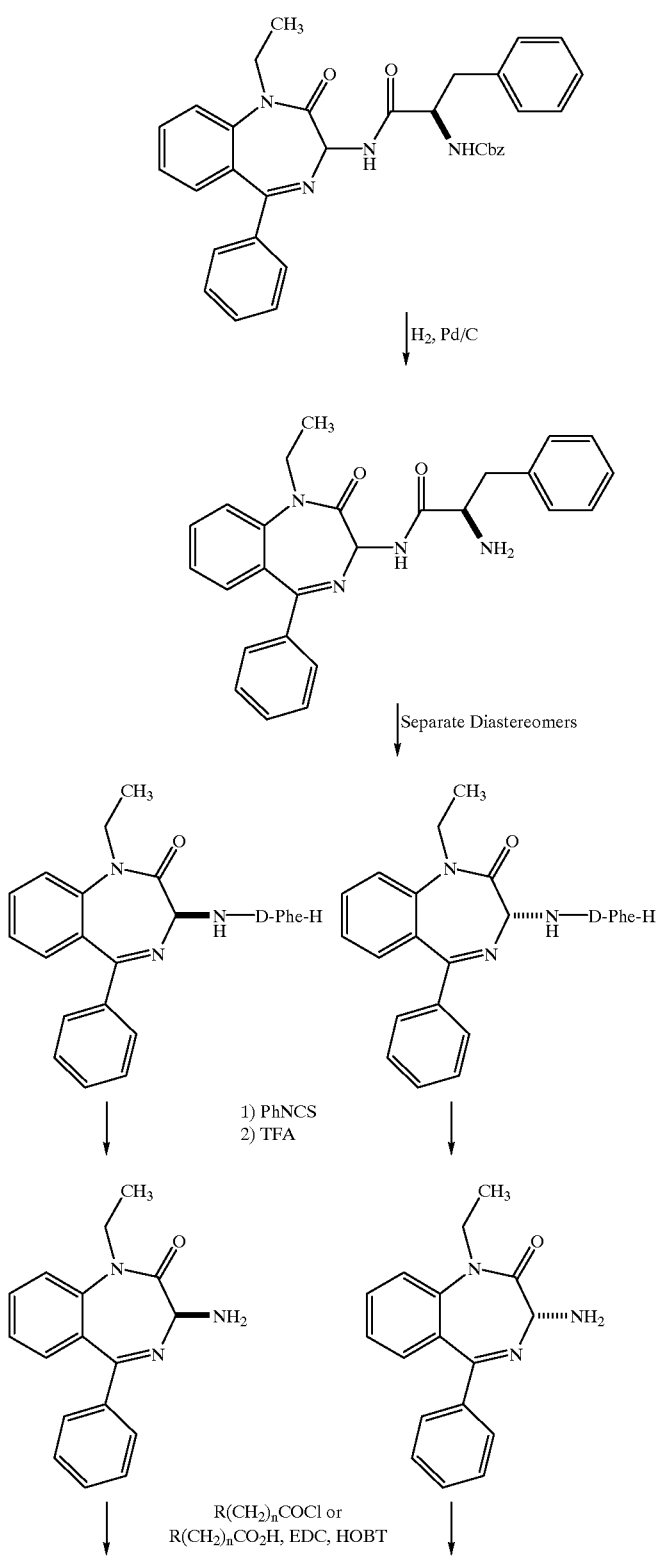

-continued
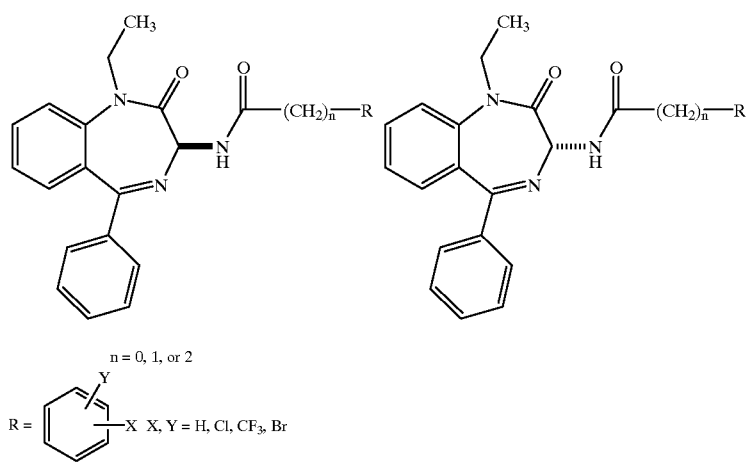
n = 0, 1, or 2
R = [phenyl with Y and X substituents]  X, Y = H, Cl, CF₃, Br
Scheme 2
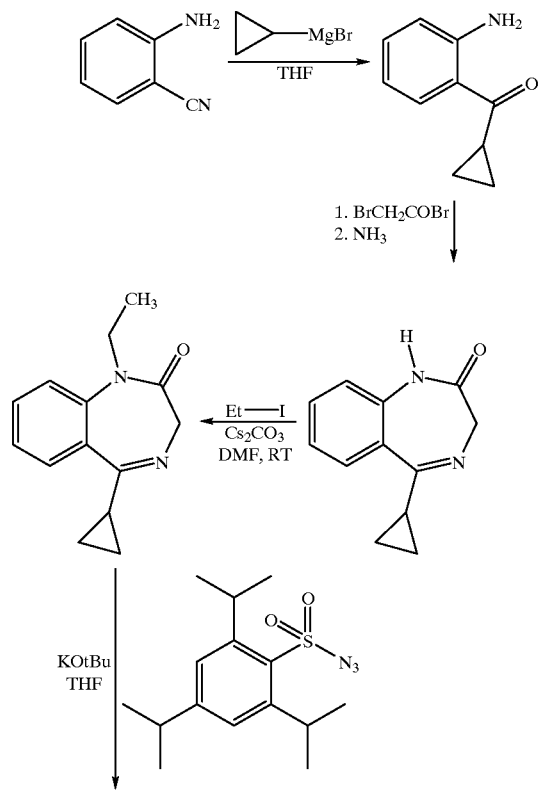

-continued

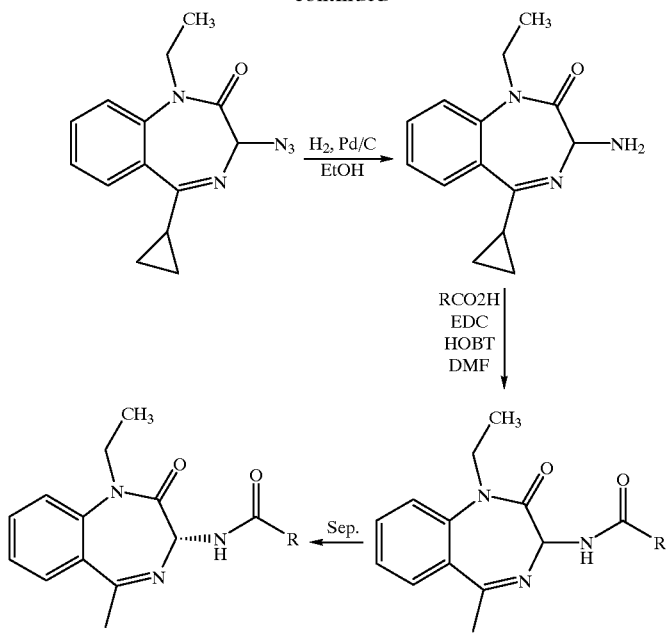

The novel compounds of the present invention, have the pharmacological properties required for antiarrhythmic agents of Class III, namely the prolongation of the myocardial action potential in vitro, without a significant depression of the Vmax, and the prolongation of QTc-interval in anesthetized dogs.

These compounds are effective in treating and preventing all types of arrhythmias including ventricular and atrial (supra-ventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 5.0 mg per kg of body weight per day in a single dose or in 2 to 4 divided doses.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, emulsions, syrups, wafers, chewing gum, or the like prepared by art recognized procedures. The amount of active compound in such therapeutically useful compositions or preparations is such that a suitable dosage will be obtained.

These compounds can be administered as the sole active ingredient or in combination with other antiarrhythmic agents or other cardiovascular agents, such as Class I, Class II or Class IV antiarrhythmic agents, vasodilators, angiotensin converting enzyme inhibitors, angiotensin II antagonists, diuretics or digitalis.

These compounds can be administered as a method of treating arrhythmia and impaired cardiac pump functions in conjunction with defibrillators, including implantable defibrillators. These compounds reduce the frequency of defibrillator firing.

Exemplary of vasodilators are compounds such as papaverine and isosorbide dinitrate. Examples of angiotensin converting enzyme inhibitors include enalapril, lisinopril and captopril. Examples of diuretics include hydrochlorothiazide and acetazolamide. The pharmaceutical agents listed herein are examples and do not represent a complete listing of the many compounds in these classes which are contemplated by this invention.

The activity of the compounds described herein as antiarrhythmic agents is measured by their ability to block the IKs and IKr currents as determined by the following test protocol.

Outward potassium currents are measured in single guinea pig ventricular myocytes using a whole-cell voltage clamp technique described in detail elsewhere (Sanguinetti and Jurkiewicz, 1990, Two components of cardiac delayed rectifier $K^+$ current: differential sensitivity to block by Class III antiarrhythmic agents. J. Gen Physiol. 96: 195–215). Myocytes are isolated by enzymatic (collagenase and protease) digestion of Langandorf perfused hearts. Single cells are then voltage clamped using 1 mm square-bore pipettes filled with 0.5 M Kgluconate, 25 mM KCl, 5 mM K(2)ATP. Cells are bathed in a solution containing, in mN: 132 NaCl, 4KCl, 1.2 MgCl[2], 10 HEPES, 10, glucose: pH 7.2, temp. 35° C.

Each cell is maintained at a holding potential of −50 mV. Test depolarizations are applied as voltage ramps from −85 to −50 mV, and as steps to −10 mV (0.5 s) and +50 mV (1.0 s). IKI is measured as peak outward current during the voltage ramp. IKr is measured as tail currents upon repolarization from −10 mV to −50 mV. IKs is measured as time-dependent current during the pulse to +50 mV. Currents are measured during control, then after exposure to drug at two different concentrations.

Employing this test the compounds described herein have an $IC_{50}$ of less than 1,000 nM as IKs blockers. The compounds of this invention are at least 10 times more potent in the blockade of IKs than the blockade of IKr.

The following examples illustrate the preparation of some of the compounds of the invention and are not to be construed as limiting the invention disclosed herein.

EXAMPLE 1

(+)-2-(2,4-bis-Trifluoromethylphenyl)-N-[2,3-dihydro-1-ethyl-2-oxo-5-phenyl-1H-1,4-benzo[e][1,4]diazepin-3-yl]acetamide

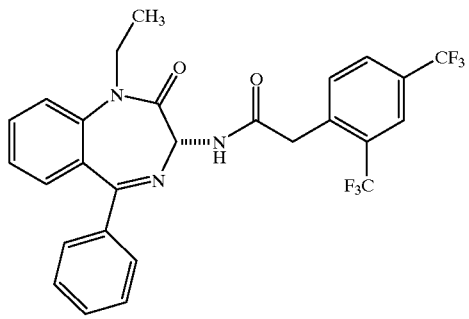

Step A

Preparation of 2,3-dihydro-1-ethyl-2-oxo-5-phenyl-1H-1,4-benzo[e][1,4]diazepine

A solution of 5-phenyl-1,4-benzo[e][1,4]diazepine-2-one (23.6 g, 0.1 mole) in DMF (100 mL) was treated with potassium carbonate (20 g, 0.14 mole) and ethyl iodide (19 g, 0.12 mole). The mixture was stirred at room temperature for five hours. The reaction mixture was then poured into water (1 L) and extracted with ethyl acetate (3×300 mL). The combined ethyl acetate fractions were dried over anhydrous magnesium sulfate, filtered and concentrated at reduced pressure to give 17.2 g of the product.

$^1$H NMR (CDCl$_3$) δ7.65–7.6(m, 2H), 7.50–7.35 (m, 3H), 7.35–7.20(m, 2H), 7.25–7.10(m, 2H), 4.79(d, J=10 Hz, 1H), 4.30 (hex, J=7.1 Hz, 1H), 3.75 (d, J=10 Hz, 1H), 3.7 (hex, J=7.1 Hz, 1H), 1.05 (t, J=7.1 Hz, 3H)

Step B

Preparation of 3-Azido-2,3-dihydro-1-ethyl-2-oxo-5-phenyl-1H-1,4-benzo[e][1,4]diazepine To a solution of 2,3-dihydro-1-(ethyl)-2-oxo-5-phenyl-1H-1,4-benzo[e][1,4]diazepine (13 g, 0.049 mole) in THF (500 mL) at −70° C. was added a solution of potassium tert-butoxide in THF (57 mL of a 1 N solution, 0.057 mole). The solution was then treated with a solution of triisopropylbenzenesulfonyl azide (16.3 g, 0.052 mole) in THF (100 mL). The reaction was stirred at −70° C. for 10 minutes and then treated with acetic acid (1 mL in 5 mL of THF) and warmed to room temperature over one hour. The reaction mixture was then poured into water (500 mL) and extracted with ethyl acetate (3×250 mL) The combined ethyl acetate fractions were washed with water (200 mL), and brine (200 mL). The ethyl acetate solution was then dried over anhydrous magnesium sulfate, filtered and concentrated at reduced pressure to afford 9.3 g of the product.

$^1$H NMR (CDCl$_3$) δ7.75–7.65(m, 2H), 7.65–7.56(m, 1H), 7.54–7.34 (m, 4H), 7.30–7.20(m, 2H), 4.52(s, 1H), 4.3(hex, J=7 Hz, 1H), 3.8(hex, J=7 Hz, 1H), 1.15 (t, J=7.0 Hz, 3H).

Step C

Preparation of racemic 3-Amino-2,3-dihydro-1-ethyl-2-oxo-5-phenyl-1H-1,4-benzo [e][1,4]diazepine To a suspension of 10% palladium on carbon (1 g) in ethyl acetate (300 mL) was added a solution of 3-azido-2,3-dihydro-1-ethyl-2-oxo-5-phenyl-1H-1,4-benzo[e][1,4]diazepine (9.1 g, 0.029 mole) in ethyl acetate (25 mL) at room temperature. Hydrogen gas was then bubbled into the reaction until the starting material was consumed (5 hr). The catalyst was filtered off and the ethyl acetate was concentrated at reduced pressure to give 7.1 g of the product.

$^1$H NMR (CDCl$_3$) δ7.65–7.50(m, 3H), 7.50–7.35(m, 4H), 7.35–7.20(m, 2H), 4.48(s, 1H), 4.3(hex, J=7.1 Hz, 1H), 3.8(hex, J=7.1 Hz, 1H), 1.15 (t, J=7.1 Hz, 3H).

Step D

Preparation of (2R)-2-Amino-3-phenyl-N-[2,3-dihydro-1-ethyl-2-oxo-5-phenyl-1H-1,4-benzo[e][1,4]diazepin-3-yl]propionamide To a stirring solution of (+)-3-amino-2,3-dihydro-1-(ethyl)-2-oxo-5-phenyl-1H-1,4-benzo[e][1,4]diazepine (7 g, 26.4 mmol) in dimethylformamide (150 mL) was added EDC (5.57 g, 29 mmol), HOBT (2.35 g, 17.4 mmol) and N-Cbz-D-phenylalanine (8.68 g, 29 mmol). The solution was stirred at ambient temperature for 2 h. The reaction was diluted with saturated aqueous sodium hydrogen carbonate (1 L) and extracted with ethyl acetate (3×300 mL). The organic layers were combined, dried with brine, anhydrous magnesium sulfate, filtered, and evaporated under reduced pressure to give an oil (15.3g) The material was dissolved in ethanol (100 mL) and added to a suspension of 10% palladium on carbon. Hydrogen gas was then bubbled into the reaction until the starting material was consumed (24 hr) The catalyst was filtered off and the ethanol was concentrated at reduced. The residue was chromatographed over silica (2.5 kg) with ethyl acetate). The faster running diastereomer was recovered as a solid (5.0 g).

$^1$H NMR, CDCl$_3$, δ9.01 (d, J=8.4 Hz, 1H), 7.64–7.19 (m, 14H), 5.55 (d, J=8.4 Hz, 1H), 4.35 (hex, J=7.1 Hz, 1H), 3.80 (hex, J=7.1 Hz, 1H), 3.70 (dd, J=3.9, 9.6 Hz, 1H), 3.35 (dd, J=3.9, 13.9 Hz, 1H), 2.82 (dd, J=9.6, 13.9 Hz, 1H), 1.27 (t, J=7.1 Hz, 1H).

Step E

Preparation of (+)-3-Amino-2,3-dihydro-1-ethyl-2-oxo-5-phenyl-1H-1,4-benzo[e][1,4]diazepine To a stirring solution of (2R)-2-amino-3-phenyl-N-[2,3-dihydro-1 ethyl 2-oxo-5-phenyl-1H-1,4-benzo[e][1,4]diazepin-3-yl]propionamide (5 g, 11.7 mmol) in methylene chloride (50 mL) was added phenyl isothiocyanate (1.5 mL, 1.66 g, 12.3 mmol) and the resulting solution was stirred for 16 h. The reaction mixture was cooled in an ice/water bath. Trifluoroacetic acid (9 mL, 13.3 g, 117 mmol) was added dropwise and the resulting solution was allowed to warm to ambient temperature over 5 hours. The reaction mixture was concentrated cold under reduced pressure to yield an oil which was chromatographed over silica (1 kg) with 90:10:1:1 methylene chloride:methanol:acetic acid:water. The pure fractions were combined and concentrated at reduced pressure and then partioned between ethyl acetate and saturated sodium bicarbonate. The organic layers were combined, dried with brine, anhydrous magnesium sulfate, filtered, and evaporated under reduced pressure to afford 2.2 g of product as a foam.

$^1$H NMR (CDCl$_3$) δ7.65–7.50(m, 3H), 7.50–7.35(m, 4H), 7.35–7.20(m, 2H), 4.48(s, 1H), 4.3(hex, J=7.1 Hz, 1H), 3.8(hex, J=7.1 Hz, 1H), 1.15 (t, J=7.1 Hz, 3H).

[a]$_D$=+145.7° (c=0.35; MeOH)

Step F

Preparation of (+)-2-(2,4-bis trifluoromethylphenyl)-N-[2,3-dihydro-1-ethyl-2-oxo-5-phenyl-1H-1,4-benzo[e][1,4]diazepin-3-yl]acetamide To a stirring solution of (+)-3-amino-2,3-dihydro-1-ethyl-2-oxo-5-phenyl-1H-1,4-benzo[e][1,4]diazepine (200 mg, 0.71 mmol) in dimethylformamide (4 mL) was added EDC (150 mg, 0.783 mmol), HOBT (95 mg, 0.71 mmol) and 2,4-bis trifluoromethylphenylacetic acid (215 mg, 0.78 mmol). This was stirred at ambient temperature for 0.5 h. The reaction was diluted with saturated aqueous sodium hydrogen carbonate (50 mL) and extracted with ethyl acetate (3×50 mL). The organic layers were combined, dried with brine, anhydrous magnesium sulfate, filtered, and evaporated under reduced pressure to give a colorless oil which was chromatographed over silica with 25 to 50% ethyl acetate/hexane. The resulting foam was crystallized from ethyl acetate/hexane to give a solid (320 mg).

$[a]_D$=+24.6° (c=0.45; MeOH), $^1$H NMR, CDCl$_3$, δ7.95 (br s, 1H), 7.84–7.70 (m, 2H), 7.60–7.20 (m, 9H), 5.49 (d, J=8.2 Hz, 1H), 4.32 (hex, J=7.1 Hz, 1H), 3.90 (br s, 2H), 3.78 (hex, J=7.1 Hz, 1H), 1.12 (d, J=7.1 Hz, 3H). Anal. Calcd. for C$_{27}$H$_{21}$F$_6$N$_3$O$_2$.0.1 EtOAc. 0.35 H2O: C, 59.99; H, 4.13; N, 7.66.

Found: C, 60.61; H, 3.85; N, 7.65%.

EXAMPLE 2

The following compound was prepared in the same manner as Example 1.

(+)-3,5-bis trifluoromethyl-N-[2,3-dihydro-1-ethyl-2-oxo-5-phenyl-1H-1,4-benzo[e][1,4]diazepin-3-yl]acetamide

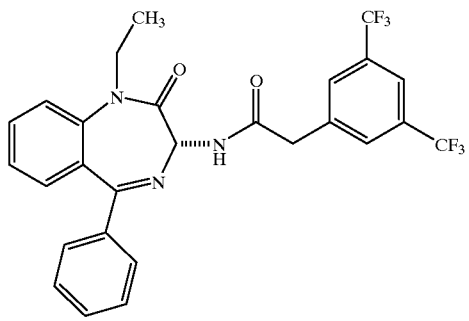

$[\alpha]_D$=+23.4° (c=0.49; MeOH)

$^1$H NMR, CDCl$_3$, δ7.84–7.78 (m, 3H), 7.60–7.20 (m, 9H), 5.51 (d, J=7.9 Hz, 1H), 4.32 (hex, J=7.1 Hz, 1H), 3.84 (br s, 2H), 3.79 (hex, J=7.1 Hz, 1H), 1.14 (d, J=7.1 Hz, 3H).

Anal. Calcd. for C$_{27}$H$_{21}$F$_6$N$_3$O$_2$.0.05 EtOAc. 0.6 H2O: C, 59.54; H, 4.15; N, 7.71.

Found: C, 59.55; H, 3.95; N. 7.70%.

EXAMPLE 3

(−)-2-(2,4-Bis-trifluoromethylphenyl)-N-[2,3-dihydro-1-ethyl-2-oxo-5-cyclopropyl-1H-1,4-benzo[e][1,4]diazepin-3-yl]acetamide

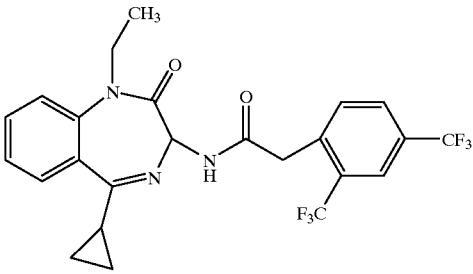

Step A 5-cyclopropyl-1,4-benzo[e][1,4]diazepin-2-one

To a solution of anthranilonitrile (85 g, 0.720 mole) in THF (1.0 L) at −10° C was slowly added a 1.6 M solution of cyclopropyl magnesium bromide in THF (1.55 L, 2.48 mole). The reaction was allowed to stir overnite at room temperature then slowly quenched into a −10° C. solution of 4N HCL (1.2 L). The mixture was stirred for 1 hour at room temperature and the pH adjusted to 7.5 with 10N sodium hydroxide. The THF layer was removed, the aqueous layer washed with ethyl acetate (800 mL), and the organic extracts concentrated in vacuo to an oil. The oil was dissolved in methylene chloride (1.2 L), washed with water (500 mL), dried over sodium sulfate, and filtered. To the methylene chloride filtrate at 0° C. was slowly added bromoacetyl bromide (168.0 g, 0.836 mole) followed by 3N sodium hydroxide (800 mL). The reaction was allowed to stir for 1 hour and the pH of the mixture adjusted to 7.5 with concentrated hydrochloric acid. The methylene chloride layer was removed and the aqueous layer washed with methylene chloride (1.0 L). The methylene chloride extracts were washed with 5% aqueous sodium bicarbonate, dried over sodium sulfate, filtered and concentrated to an oil. The oil was dissolved in ethanol (1.5 L) added to a 50% solution of ethanol/ aqueous ammonium hydroxide (6.3 L) and allowed to stir for 48 hours. The reaction mixture was concentrated in vacuo to 2.7 L and the pH adjusted to 12.0 with 50% sodium hydroxide. After stirring at pH 12 for 1 hour, the reaction pH was adjusted to 8.5 with concentrated hydrochloric acid and the solids were filtered. The cake was washed with water (1.0 L), sucked dry and dried in vacuo at 40° C. to give 102.2 g of 5-cyclopropyl-1,4-benzo[e][1,4]diazepine-2-one. MP—192–193° C.

$^1$H NMR (CDCl$_3$, 300 MHz) δ9.45 (s, 1H) 7.84 (dd, J=8.0 and 1.6 Hz,1H), 7.45 (dt, J=8.0 and 1.6 Hz, 1H), 7.24 (dt, J=8.0 and 1.6 Hz,1H), 7.12 (dd, J=8.0 and 1.6 Hz, 1H),4.04 (br s. 2H), 1.95 (m,1H), 0.9–1.2 (m, 4H)

Step B

Preparation of 2,3-dihydro-1-ethyl-2-oxo-5-cyclopropyl-1H-1,4-benzo[e][1,4]diazepine A solution of 5-cyclopropyl-1,4-benzodiazepine-2-one (50 g, 0.250 mole) in DMF (250 mL) was treated with cesium carbonate (122 g, 0.375 mole), cooled to 0° C. and iodoethane (47.2 g, 0.30 mole) added. The mixture was stirred at 25° C. overnight. The reaction was cooled to room temperature and filtered. The solids were washed with ethyl acetate (2 L) and the filtrates diluted with water (2 L). The pH was adjusted to 7.6 with 10% aqueous potassium hydrogen sulfate and the organic layer removed. The aqueous layer was washed with ethyl acetate (1 L) and combined ethyl acetate extracts washed with water (500 mL). The ethyl acetate extracts were dried over sodium sulfate, filtered and concentrated in vacuo to yield 57.5 g of an oil. The oil was taken up in toluene (200 mL) and concentrated. The oil was used in the next step without further purification.

Step C

Preparation of 3-azido-5-cyclopropyl-1-ethyl-1H-benzo[e][1,4]diazepine

To a stirring solution of 5-cyclopropyl-1-ethyl-1H-benzo[e][1,4]diazepine (6.4 g, 0.028 mol) in THF (125 ml) cooled to −78° C. was added potassium tert-butoxide (2.05 eq, 0.057 mol, 57.2 ml of a 1 M solution in THF) dropwise over 15 min. A solution of 2,4,6-triisopropylphenyl-sulfonylazide (9.5 g, 0.031 mol) in THF (100 ml) was added over 5 min. The solution was stirred for 10 min, acetic acid (7.7 ml,0.123 mol) was added and the reaction warmed to 30° C. for 2 hour. The reaction was concentrated the residue dissolved in dichloromethane (200 mL) and washed with satd. NaHCO$_3$ (200 ml). The aqueous layer was back extracted with dichloromethane (100 ml). The organic layers were combined, dried with Na$_2$SO$_4$ and evaporated to a foam. The foam was chromatographed over silica eluting with 30% ethyl acetate-:hexane. The appropriate fractions were collected and evaporated under reduced pressure to give 5.83 g of a powder. MP=158–160° C.

Step D

Preparation of 3-amino-5-cyclopropyl-1-ethyl-1H-benzo[e][1,4]diazepine

To a stirred solution of 3-azido-5-cyclopropyl-1-ethyl-1H-benzo[e][1,4]diazepine (5.8 g, 21.5 mmol) in ethanol (500 mL) under argon was added 10% palladium on charcoal (1.0 gm). The argon was displaced with hydrogen and the mixture was vigorously stirred for 45 min (1 atm hydrogen). The reaction was filtered and the filtrate concentrated in vacuo to an oil (5.3 gm, 100%) which solidified upon standing. MP 93–95° C.

Step E

Preparation of: (+,−)-2-(2,4-bis-trifluoromethylphenyl)-N-[2,3-dihydro-1-ethyl-2-oxo-5-cyclopropyl-1H-1,4-benzo [e][1,4]diazepin-3-yl]acetamide To a stirring solution of 3-amino-5-cyclopropyl-1-ethyl-1H-benzo[e][1,4] diazepine (0.10 g, 0.409 mmole) in DMF (2 mL) was added 1-hydroxybenztriazole hydrate (88 mg, 0.573 mmol), 2,4-bis-trifluoromethylphenylacetic acid (111 mg, 0.45 mmol), triethylamine (80 L, 0.573 mmole), and (1-(3-dimethylaminopropyl-3-ethylcarbodiimide (110 mg, 0.573 mmol). The solution was stirred at ambient temperature for 2 hours. The reaction was diluted with 10% citric acid (20 mL) and extracted with ethyl acetate (2×40 mL) . The combined organics were washed with 10% sodium bicarbonate (20 mL) dried over Na$_2$SO$_4$, and evaporated to a foam. The foam was chromatographed using a Chiralpak AD® preparative HPLC column (Chiral Technology, 25×2 cm) eluting with ethanol/hexane(1/1, 6 mL/min). The pure fractions were collected and evaporated under reduced pressure to give 95 mg of the (+) enantiomer and 95 mg of the (−) enantiomer as foams. The enantiomers were crystallized from ether/hexane to give 80 mg (+) enantiomer and 80 mg (−) enantiomer as solids.

(+)enantiomer $^1$H NMR (CDCl$_3$, 300 MHz) δ7.90 (s, 1H), 7.78 (d, J=8.6 Hz, 2 H),7.68 (d, J=8.6 Hz,1H), 7.54(dt, J=8.6 and 1.6 Hz, 1H), 7.32 (t, J=8.6, 1 H), 7.29 (d, J=8.6 Hz, 1H), 7.18 (br d, J=8.6 Hz,1 H), 5.24 (d, J=8.6 Hz,1 H), 4.15 (sextet, J=8.7 Hz, 1H), 3.89 (s, 2H), 3.75 (sextet, J=8.7 Hz, 1H), 1.95 (m, 1 H), 1.12 (t, J=8.5 Hz,3H), 0.8–1.1 (m, 4H).

Analysis Calcd. for C$_{24}$H$_{21}$F$_6$N$_3$O$_2$: C, 57.95; H, 4.26; N, 8.45;

Found: C, 58.13; H, 4.34; N, 8.12.

mp=124–125° C., [α]$_D$=+19.2° (MeOH), (−)enantiomer $^1$H NMR (CDCl$_3$, 300 MHz) δ7.90 (s, 1H), 7.78 (d, J=8.6 Hz, 2 H),7.68 (d, J=8.6 Hz,1H), 7.54(dt, J=8.6 and 1.6 Hz, 1H), 7.32 (t, J=8.6, 1 H), 7.29 (d, J=8.6 Hz, 1H), 7.18 (br d, J=8.6 Hz,1 H), 5.24 (d, J=8.6 Hz,1 H), 4.15 (sextet, J=8.7 Hz, 1H), 3.89 (s, 2H), 3.75 (sextet, J=8.7 Hz, 1H), 1.95 (m, 1 H), 1.12 (t, J=8.5 Hz,3H), 0.8–1.1 (m, 4H).

Analysis Calcd. for C$_{24}$H$_{21}$F$_6$N$_3$O$_2$: C, 57.95; H, 4.26; N, 8.45;

Found: C, 57.83; H, 4.25; N, 8.10.

mp=124–125° C., [α]$_D$=−19.3° (MeOH),

Following procedures similar to those described above for the preparation of Examples 1–3, the following compounds were prepared:

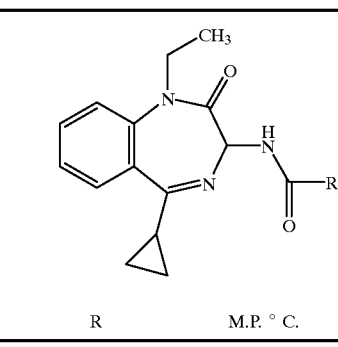

| Ex. # | R | M.P. ° C. | Stereochemistry |
|---|---|---|---|
| 4a | 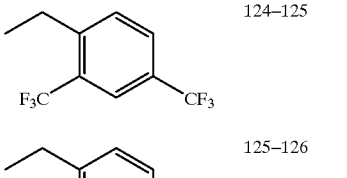 | 124–125 | (+) |
| 4b | 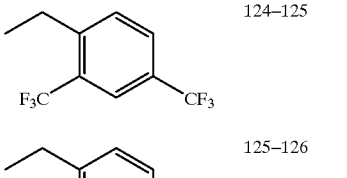 | 125–126 | (−) |
| 5a | 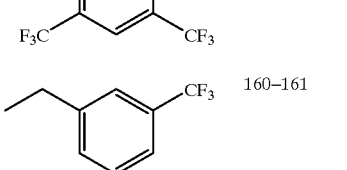 | 160–161 | (+) |
| 5b | 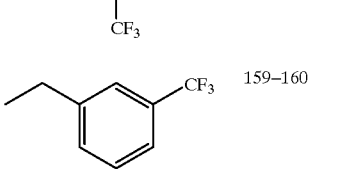 | 159–160 | (−) |

-continued
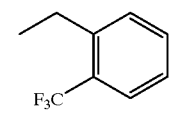
| Ex. # | R | M.P. °C. | Stereochemistry |
|---|---|---|---|
| 6a | 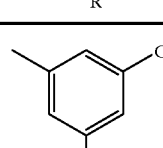 | 146–147 | (+) |
| 6b | 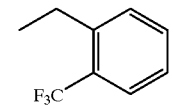 | 144–145 | (−) |
| 7a | 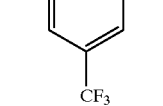 | 118–120 | (+) |
| 7b | 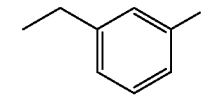 | 119–120 | (−) |
| 8a | 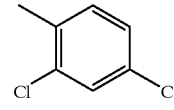 | 200–201 | (+) |
| 8b | 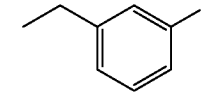 | 198–200 | (−) |
| 9a | 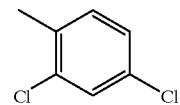 | 115–116 | (+) |
| 9b | 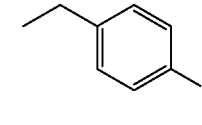 | 114–115 | (−) |
| 10a | 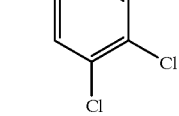 | 173–175 | (+) |
-continued
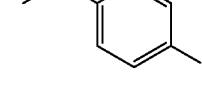
| Ex. # | R | M.P. °C. | Stereochemistry |
|---|---|---|---|
| 10b | 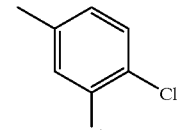 | 174–175 | (−) |
| 11a | 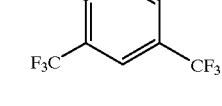 | 115–116 | (+) |
| 11b | 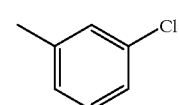 | 115–116 | (−) |
| 12a | 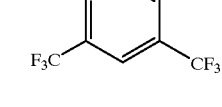 | 130–132 | (+) |
| 12b | 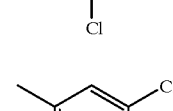 | 135–136 | (−) |
| 13a | 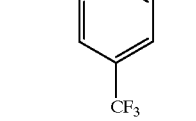 | 157–159 | (+) |
| 13b | 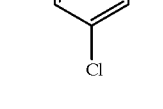 | 157–158 | (−) |
| 14a | 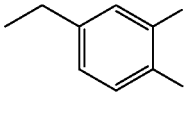 | 107–109 | (+) |

-continued

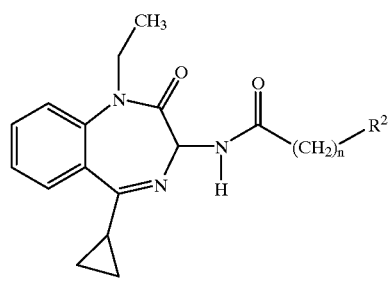

| Ex. # | R | M.P. ° C. | Stereochemistry |
|---|---|---|---|
| 14b | (3-ethyl-2-CF₃-6-CH₃-phenyl) | 107–108 | (−) |

What is claimed is:

1. A compound of the formula

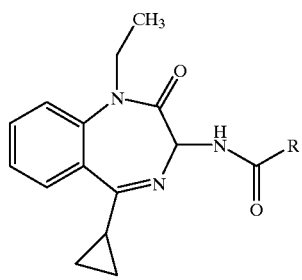

wherein

R² is
1) phenyl, or
2) substituted phenyl, with one or two substituents, selected from the group consisting of
   a) —Cl, Br, F, or I,
   b) —CF₃, and
   c) —C$_{1-3}$ alkyl, and
n is 0, 1 or 2, or a pharmaceutically acceptable addition salt and/or hydrate thereof, or crystal form thereof, or where applicable, a geometric or optical isomer or racemic mixture thereof.

2. The compound according to claim 1 of the formula where R is indicated in the table below:

| Ex. # | R | Stereochemistry |
|---|---|---|
| 4a | 2-ethyl-3,5-bis(CF₃)phenyl | (+) |
| 4b | 2-ethyl-3,5-bis(CF₃)phenyl | (−) |
| 5a | 3-ethyl-5-CF₃-(CF₃)phenyl | (+) |
| 5b | 3-ethyl-5-CF₃-(CF₃)phenyl | (−) |
| 6a | 2-ethyl-6-CF₃-phenyl | (+) |
| 6b | 2-ethyl-6-CF₃-phenyl | (−) |
| 7a | 3-ethyl-5-CF₃-phenyl | (+) |
| 7b | 3-ethyl-5-CF₃-phenyl | (−) |
| 8a | 4-ethyl-?-CF₃-phenyl | (+) |
| 8b | 4-ethyl-?-CF₃-phenyl | (−) |
| 9a | 4-methyl-2,5-bis(CF₃)phenyl | (+) |

-continued
| Ex. # | R | Stereochemistry |
|---|---|---|
| 9b | 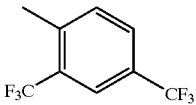 | (−) |
| 10a | 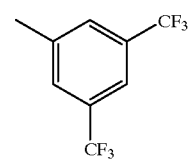 | (+) |
| 10b | 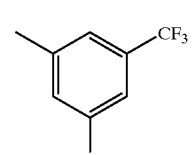 | (−) |
| 11a | 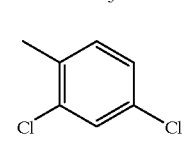 | (+) |
| 11b | 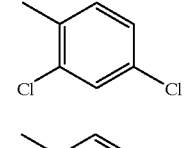 | (−) |
| 12a | 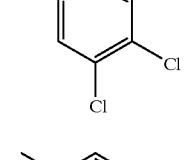 | (+) |
| 12b | 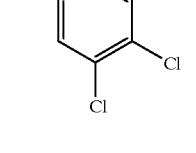 | (−) |
-continued
| Ex. # | R | Stereochemistry |
|---|---|---|
| 13a | 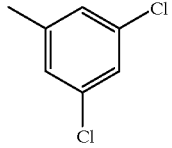 | (+) |
| 13b | 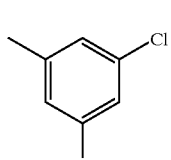 | (−) |
| 14a | 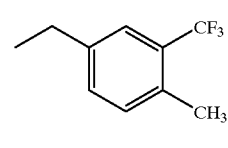 | (+) |
| 14b | 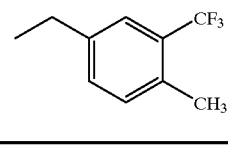 | (−) |
3. A pharmaceutical composition, which comprises an effective amount of the compound of claim 1 and an acceptable carrier therefor.
4. A process for making a pharmaceutical composition comprising combining a compound of claim 1 and a pharmaceutically acceptable carrier.
* * * * *